United States Patent
Muhl et al.

(10) Patent No.: US 7,523,006 B2
(45) Date of Patent: Apr. 21, 2009

(54) MEASUREMENT SENSOR ASSEMBLY AND METHOD FOR MEASURING THE QUALITY OF A FLUID

(75) Inventors: Mike Muhl, Freiburg (DE); Jürgen Hall, Friedensweiler/Rötenbach (DE)

(73) Assignee: Testo GmbH & Co. (DE)

(*) Notice: Subject to any disclaimer, the term of this patent is extended or adjusted under 35 U.S.C. 154(b) by 197 days.

(21) Appl. No.: 10/501,578

(22) PCT Filed: Dec. 19, 2002

(86) PCT No.: PCT/EP02/14585

§ 371 (c)(1),
(2), (4) Date: Feb. 24, 2005

(87) PCT Pub. No.: WO03/060499

PCT Pub. Date: Jul. 24, 2003

(65) Prior Publication Data

US 2005/0222783 A1    Oct. 6, 2005

(30) Foreign Application Priority Data

Jan. 17, 2002    (DE) ................. 102 02 002

(51) Int. Cl.
*G01F 17/00*    (2006.01)
*G01F 23/00*    (2006.01)
*G01L 7/00*    (2006.01)
*G01N 11/00*    (2006.01)

(52) U.S. Cl. ............... 702/52; 702/55; 73/335.02; 73/304 C; 324/663

(58) Field of Classification Search ............... 702/55, 702/52; 73/335.02–335.05, 64.55, 304 C; 324/663
See application file for complete search history.

(56) References Cited

U.S. PATENT DOCUMENTS 3,639,835 A  *  2/1972  Dammig et al. ............ 324/686
4,510,436 A  *  4/1985  Raymond ................ 324/690

(Continued)

FOREIGN PATENT DOCUMENTS

DE    100 15 516 A1    11/2000

(Continued)

OTHER PUBLICATIONS

Balendonck et al., 'Application of an Intelligent Dielectric Sensor for Soil Water Content, Electrical Conductivity and Temperature', May 2001, IEEE Publication, pp. 1817-1822.*

(Continued)

*Primary Examiner*—Edward Raymond
*Assistant Examiner*—Elias Desta
(74) *Attorney, Agent, or Firm*—Muirhead and Saturnelli, LLC

(57) ABSTRACT

The aim of the invention is to provide a simple and reliable method of measuring the quality of a fluid (2), in particular an oil or fat. This is achieved by a dielectric measurement in conjunction with a temperature measurement, which are carried out in situ by means of a measuring assembly and a sensor assembly (1) used with the latter, whereby the sensor assembly is submerged in the fluid. This permits information concerning the condition of the fluid, in particular concerning the age of the frying oil or fat, to be obtained in a rapid, low-cost manner.

32 Claims, 3 Drawing Sheets

U.S. PATENT DOCUMENTS

| | | | | |
|---|---|---|---|---|
| 5,269,175 A | * | 12/1993 | Chmiel et al. | 73/53.05 |
| 5,423,206 A | * | 6/1995 | Hetzel | 73/61.77 |
| 5,818,731 A | | 10/1998 | Mittal et al. | |
| 5,929,754 A | * | 7/1999 | Park et al. | 340/439 |
| 5,994,906 A | * | 11/1999 | Morgan et al. | 324/633 |
| 6,028,433 A | * | 2/2000 | Cheiky-Zelina et al. | 324/663 |
| 6,138,508 A | * | 10/2000 | Hannan et al. | 73/304 C |
| 6,250,152 B1 | | 6/2001 | Klein et al. | |
| 6,320,393 B1 | * | 11/2001 | Yasui et al. | 324/663 |
| 6,469,521 B1 | | 10/2002 | Klün et al. | |

FOREIGN PATENT DOCUMENTS

| | | |
|---|---|---|
| EP | 0 405 587 A | 1/1991 |
| EP | 1 046 908 A2 | 10/2000 |
| FR | 2 792 414 A | 10/2000 |
| JP | 2000 338074 | 12/2000 |

OTHER PUBLICATIONS

Patent Abstracts of Japan; vol. 012, No. 488 (P-803), Dec. 20, 1988 & JP 63 200051 A (Horiba Ltd; Others: 01), Aug. 18, 1988 abstract.

* cited by examiner

MEASUREMENT SENSOR ASSEMBLY AND METHOD FOR MEASURING THE QUALITY OF A FLUID

FIELD OF THE INVENTION

The present invention may be used in measurement technology, in particular for measuring the properties of fluids. Certain properties may be determined on the basis of measurable dielectric properties by using the present invention, in particular in the case of oils, in particular liquid deep-frying fats.

The present invention relates to a measuring system for determining a property, in particular the aging condition of a fluid, in particular a deep-frying fat, from a dielectric property of the fluid using a first sensor to measure an electric capacitance and a second sensor to measure the temperature.

In addition, the present invention also relates to a sensor system for measuring a dielectric property of a fluid by using a dielectric sensor which may be immersed in the fluid and has a measuring capacitor designed as a stray-field capacitor.

BACKGROUND OF THE INVENTION

It is known that oils used for edible purposes as well as those used industrially for mechanical applications are subject to an aging process which is influenced by high temperatures, among other things. Various chemical reactions take place, altering the quality of the particular oil.

Oil is frequently evaluated first on the basis of the visual impression, i.e., a decline in optical transmittance, or increasing discoloration over a period of time.

However, this variable is only a single parameter which is not generally sufficient for evaluating quality.

For example, a loss of quality in deep-frying fat is often discernible on the basis of other parameters even before there is any visible discoloration and may necessitate replacement of the fat.

The relevant quality of an oil may be ascertained, for example, by chemical tests, also in combination with visual tests.

For some time now, it has also been known that the aging condition of an oil may be evaluated on the basis of the measured dielectric constant.

One problem here is the fact that the dielectric constant also depends on the temperature. To solve this problem, for example, it is possible to provide for an oil sample to be heated or cooled to a fixedly predetermined temperature so that a dielectric measurement may be performed at this temperature. Such a measuring method is taken into account in U.S. Pat. No. 5,818,731, for example, as the related art.

The above publication also describes measuring methods by which the quality of an oil is to be determined by using several measured physical parameters such as a dielectric measured variable and the viscosity of the oil.

Since the color of a deep-frying fat is one of the most sensitive variables for determining its quality, U.S. Pat. No. 5,818,731 proposes combining a measurement of the dielectric constant with a measurement of optical transmittance in a certain wavelength range to perform a comprehensive evaluation of the quality of oil. To do so, a sample of an oil is placed in a graduated container, where it is exposed to light of a wavelength of 675 nanometers from a laser diode to measure the transmittance in this wavelength range. In addition, a measuring capacitor is used to measure the dielectric constant. This measurement is performed after the sample has been heated to a temperature between 155° C. and 185° C.

After the dielectric constant has been measured, the measured dielectric constant is converted to the value at a standard temperature between 155° C. and 185° C. with the help of a temperature measurement and a stored regression curve on the basis of the known temperature dependence. This value should then allow a conclusion to be drawn regarding the quality of the fat in conjunction with the measured transmittance.

One disadvantage of the known measuring systems is that the measuring time amounts to several minutes up to approximately ten minutes and a certain quantity of the oil used must be taken as a sample and warmed to perform the measurement. The specimen container must then be cleaned thoroughly for a new measurement.

Accordingly, it is desirable to create a measuring system and a sensor system so that they will be simple to construct and will allow a rapid determination of the quality of the particular fluid while being easy and uncomplicated to operate.

SUMMARY OF THE INVENTION

A measuring system according to one aspect of the present invention includes a first sensor that is designed as a dielectric sensor having a stray-field capacitor which functions as the measuring capacitor and is immersible in the fluid, while a second sensor is designed as a temperature sensor that is immersible in the fluid.

Due to the fact that the dielectric constant and the temperature are measured, basically a statement regarding the condition and properties of the particular fluid may be derived. The design of the sensors as immersible sensors allows the measurement to be performed in situ without having to take a sample to place into a measuring system. This shortens the measuring time since there is no need for sampling but also because the measurement is performed at the temperature prevailing in the fluid volume without a change in temperature. Although this makes analysis of measured values more demanding, the measuring procedure itself becomes simpler and quicker to perform. In the analysis, the particular temperature at which the measurement is performed must be taken into account when the measured dielectric constant is analyzed to draw a conclusion regarding the quality of the fluid.

Such a measuring system is readily portable and may be used directly for performing measurements in containers in which the fluid is used, e.g., in fryers. Such measuring systems may also be installed permanently in deep fryers for checking the deep-frying fat used and/or such equipment may be retrofitted with such a measuring system.

According to an advantageous embodiment of the present invention, the first and second sensors are connected to an analyzer device which assigns a value of the property to be determined to a measured temperature value and a measured electric capacitance value.

Either a computational algorithm or a value matrix may be stored in the analyzer device, so that a quality value of the fluid, e.g., the aging condition of a deep-frying fat, may be assigned to the temperature and capacitance values measured in each, i.e., the dielectric constant resulting from them. For example, a concentration of certain polar substance components in the fluid may be determined via values determined empirically in advance from the dielectric constant and the temperature at which the dielectric constant was measured, and this concentration may in turn permit an inference regarding the aging condition of the fluid.

According to another advantageous embodiment of the present invention, the value of the electric capacitance measured by the dielectric sensor is compared in a comparator device of the analyzer device with a stored reference value assigned to the measured temperature value and a signal is output when the reference value is reached or exceeded.

In this case the analyzer device contains a value of the measured capacitance and/or the dielectric constant determined from it which is still justifiable with respect to the resulting aging condition of the fluid for each temperature value at which a measurement may be performed, i.e., between 30° C. and 200° C. in increments of 0.5° C. or 1° C. If this value as a reference value is exceeded, the analyzer device outputs a signal after the comparison, warning the user, e.g., in the form of a visual or acoustic warning signal.

The present invention may also be embodied advantageously by a compensation device for correcting the measured value of the electric capacitance, taking into account a measured reference value of a capacitance measured on an auxiliary capacitor located in the vicinity of the measuring capacitor.

The dielectric constant of the fluid is determined by determining the influence of the fluid on the stray-field capacitor, which serves as a measuring capacitor when the latter is immersed in the fluid. A high dielectric constant of the fluid results in an increase in the electric capacitance of the measuring capacitor. However, it should be taken into account here that interfering influences going beyond immersion of the measuring capacitor in the fluid may also occur in measuring the capacitance. For example, there is a capacitance between the feeder lines of the measuring capacitor which may be affected by external influences. If the feeder lines of the measuring capacitor are immersed in the fluid, the capacitance between them also increases, which results in an interference in the capacitance measurement to be performed on the measuring capacitor itself. For this reason, an auxiliary capacitor is provided, its capacitance changing in the same sense as the capacitance of the feeder lines of the measuring capacitor, e.g., when the measuring capacitor is immersed too far into the fluid. If the capacitance of the auxiliary capacitor is monitored, an increase in the electric capacitance of the auxiliary capacitor means that the capacitor is immersed in the fluid. This results in the need for compensation of the measurement on the measuring capacitor. The capacitance measured there is distorted by the effects on the feeder line and must be compensated accordingly.

The compensation may also provide for the sensor to be pulled a certain distance out of the fluid until the capacitance of the auxiliary capacitor corresponds to the normal value when an increase in the capacitance of the auxiliary capacitor is observed. This ensures that even the feeder lines of the measuring capacitor do not protrude into the fluid.

However, other ambient influences on the feeder lines of the measuring capacitor and/or on the measuring capacitor itself, e.g., temperature influences which go beyond the dependence of the dielectric constant of the fluid on the temperature, may also be compensated by taking into account the behavior of the auxiliary capacitor.

Furthermore, according to an advantageous embodiment of the present invention, in the case of a sensor system for measuring a dielectric property of a fluid with a dielectric sensor immersible in the fluid having a measuring capacitor designed as a stray-field capacitor, the sensor has an auxiliary capacitor, and when the sensor is introduced into the fluid, the auxiliary capacitor is not immersed in the fluid until the measuring capacitor has been fully immersed in the fluid.

Such a sensor system is optimally used in the sense described above for the measuring system which is also the object of the present invention. For the best possible compensation, the feeder lines of the measuring capacitor and the auxiliary capacitor may be designed to be symmetrical and of the same design. They are then subject to the same interfering influences in the same way.

In addition, the sensor system according to the present invention may be designed so that the auxiliary capacitor is made up of two spur lines that end upstream from the measuring capacitor and are designed and situated like the feeder lines to the measuring capacitor. Any interference that might act on both feeder lines equally may be compensated optimally, e.g., by subtraction of the measured values, due to the symmetry of the feeder lines of the measuring capacitor and the auxiliary capacitor.

According to another advantageous embodiment of the sensor system according to the present invention, the measuring capacitor is formed by a plurality of flat conductors, e.g., in the form of an interdigital capacitor.

The sensor system may have a particularly simple design due to the fact that the conductors are printed on an insulating substrate by a thin-film or thick-film technique.

The printed conductors may be applied to a flat body or to a round or cylindrical body, for example.

The cylindrical shape is characterized in that it is particularly space saving, while the flat design requires a much shorter time for equalization of the temperature in the fluid due to the larger area of interaction with the fluid.

The temperature sensor in the sensor system according to the present invention may be designed advantageously in the form of an NTC resistor, a PCT resistor or a temperature element. These temperature sensors are inexpensive, easy to calibrate and robust, in addition to having a stable performance, so that the entire sensor system need not be calibrated too frequently.

It has proven advantageous for the temperature sensor to be connected to the dielectric sensor to form a structural unit. For example, the temperature sensor may be attached to the substrate for the printed conductors of the measuring capacitor. In this case, use of the sensor system and/or the measuring system is simplified, because only a single probe having the two sensors need be introduced into the fluid, i.e., into the deep-frying fat.

It has also proven to be advantageous for the feeder lines of the temperature sensor to be applied to the insulating substrate in the form of printed conductors. This embodiment of the sensor system is particularly inexpensive and simple to manufacture, and there is no interference in the capacitance measurements due to the feeder lines to the temperature sensor.

BRIEF DESCRIPTION OF THE DRAWINGS

The present invention is illustrated in the drawing and explained in greater detail below on the basis of an exemplary embodiment.

DETAILED DESCRIPTION OF VARIOUS EMBODIMENTS

Figure 1:
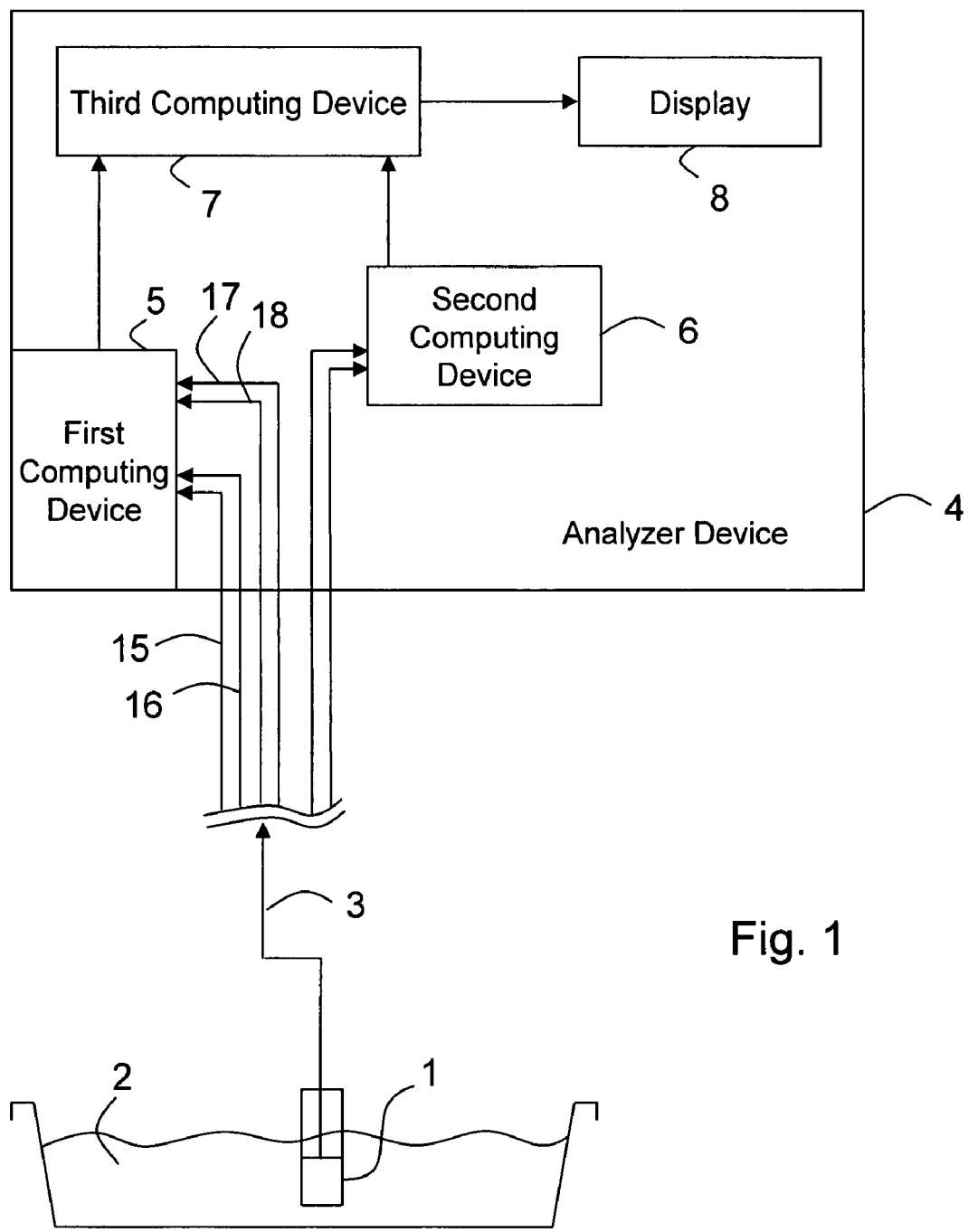
FIG. 1 schematically shows a measuring system according to the present invention in a first embodiment.

FIG. 1 schematically shows a measuring system having a sensor system 1 which is immersed in a fluid 2, e.g., a deep-frying fat. Sensor system 1 has a dielectric sensor and a temperature sensor, which are described in greater detail below.

Sensor system 1 is connected by feeder lines 3 to a digital analyzer device 4. Analyzer device 4 has a first computing device 5 in which a capacitance, a dielectric constant or a value corresponding to these values is determined from the measured data. In a second computing device 6, the temperature of the fluid is determined from the data supplied by the temperature sensor.

In a third computing device 7, a temperature-independent value of the dielectric constant is assigned to the value of the dielectric constant and the measured temperature, representing an objective criterion for the condition of the fluid, namely in this case the aging condition of the deep-frying fat. This may be, for example, a value based on a fixed temperature. The value determined in this way is shown on a display 8 and is output to the user. Instead of display 8, an interface may also be provided for transferring data to another data processing device.

Figure 2:
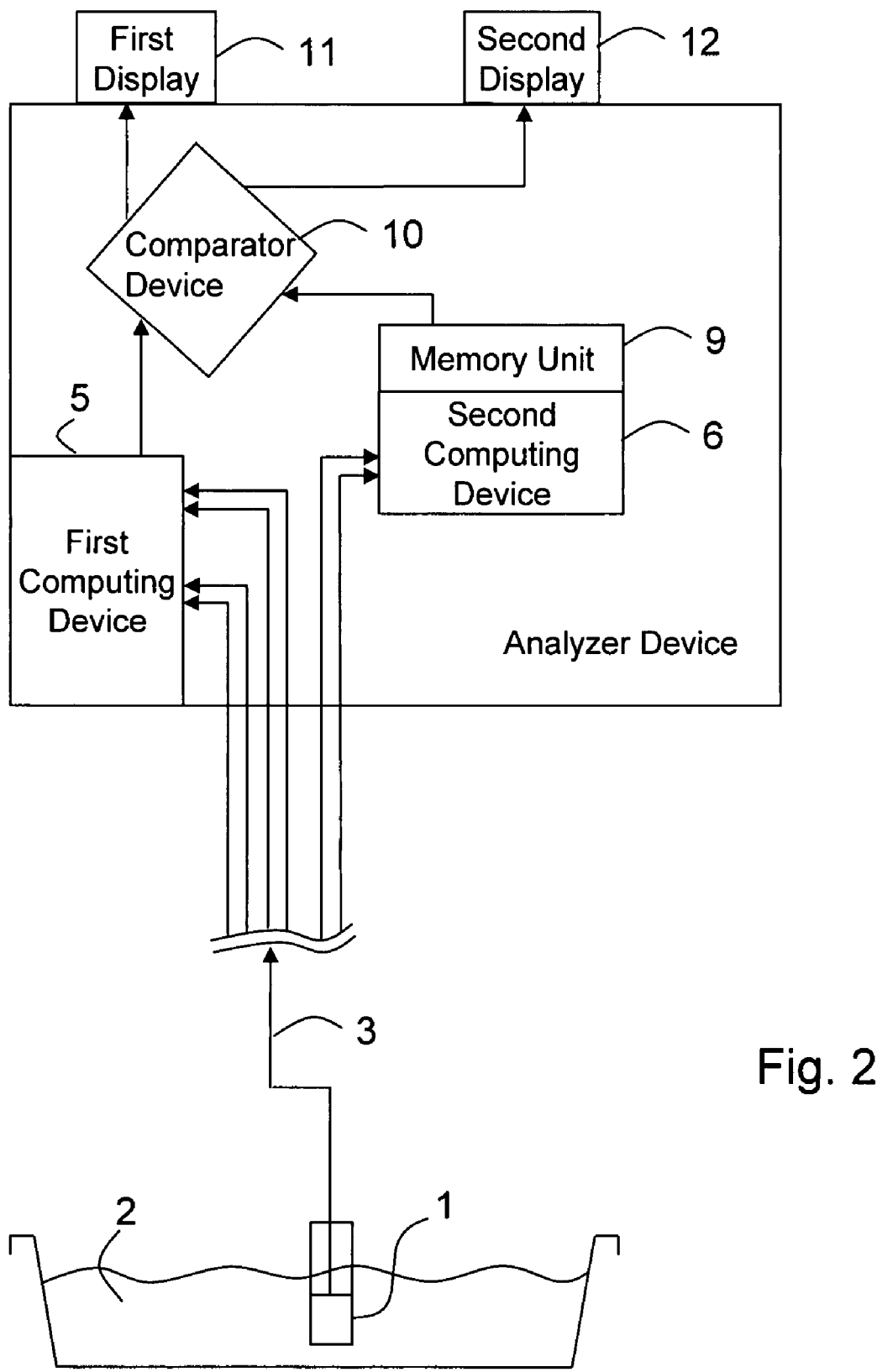
FIG. 2 schematically shows the measuring system according to the present invention in the second embodiment.

FIG. 2 shows a similar measuring system like that in FIG. 1, where the same elements are labeled with the same reference numerals as in FIG. 1.

As in the example described above, the dielectric constant or a corresponding variable is determined in the first computing device. The temperature is determined in second computing device 6.

In addition, in second computing device 6, a certain dielectric constant, which is still just allowed at the particular temperature, or a corresponding value, e.g., the measured capacitance for the deep-frying fat to be measured, is allocated to the temperature on the basis of the stored reference data for various temperature values. The reference data is stored in a memory unit 9. The value of the dielectric constant determined by first computing device 5 or the corresponding variable is compared with the reference variable which is still allowed in comparator device 10 and is assigned to the measured temperature by second computing device 6. The comparison is evaluated by an appropriate first display device 11 being activated when the two values match or when the value found is less than the reference value, indicating that the deep-frying fat is still acceptable and usable.

If the dielectric constant determined by first computing device 5 or the corresponding variable exceeds the assigned reference value, second display device 12 is then activated, indicating that the deep-frying fat should no longer be used and should be replaced. First display device 11 may be designed, for example, as a green light, with second display device 12 being designed as a red light. Comparator device 10 may also be set up so that the deep-frying fat is discarded as soon as the measured value for the dielectric constant matches the reference value and the need for replacement is displayed by the second display device.

Figure 3:
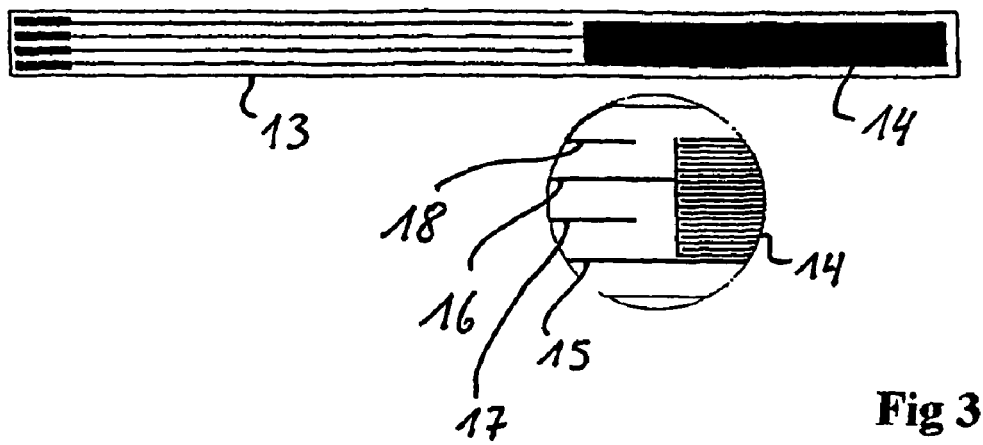
FIGS. 3, 4 and 5 show various embodiments of a dielectric sensor, in FIG. 5 a dielectric sensor having a temperature sensor.
Figure 4:
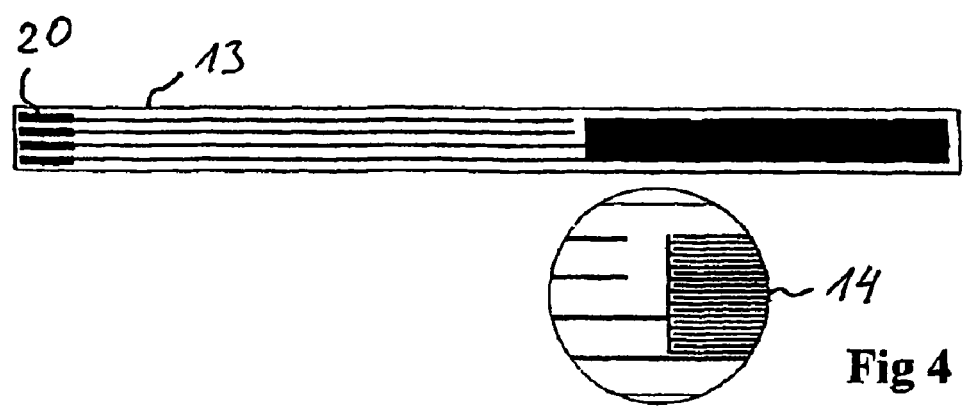
Figure 5:
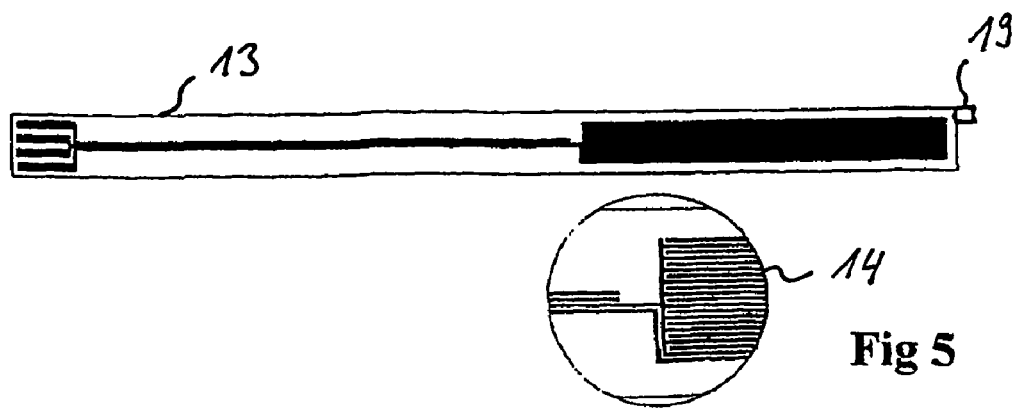

The following discussion describes in greater detail how the measured values for the dielectric constant and the temperature are obtained. Reference is made first to FIGS. 3, 4 and 5. FIG. 3 shows a portion of sensor system 1 illustrated in FIGS. 1 and 2 in a side view. FIG. 3 shows a flat ceramic substrate 13 on which flat printed conductors are printed by thin film technique or thick film technique. The printed conductors are advantageously composed of a noble metal, e.g., gold. The left part of the diagram shows four feeder lines which are similarly designed and run in parallel to one another.

The right part of the diagram shows measuring capacitor 14 which is designed in the form of a stray-field capacitor having intertwined coiled printed conductors in a meandering layout. The measuring capacitor is shown a second time in the enlarged detail inside the circle, where it is more discernible. It has two feeder lines 15, 16 which lead from measuring capacitor 14 to first computing device 5 of analyzer device 4.

The capacitance of measuring capacitor 14 depends on the medium in which measuring capacitor 14 is situated because the field lines of the capacitor penetrate into the immediate environment. If the measuring capacitor is immersed in a fluid having a higher dielectric constant than air, as illustrated in FIGS. 1 and 2, the capacitance of measuring capacitor 14 is then increased considerably. The increase in measured capacitance permits an inference to be drawn as to the dielectric constant of the medium surrounding measuring capacitor 14.

In addition to feeder lines 15, 16 of the measuring capacitor, feeder lines 17, 18 are provided on ceramic substrate 13, ending as blind spur lines upstream from measuring capacitor 14 and forming an auxiliary capacitor, the capacitance of which is also monitored in analyzer device 4. Changes in the environment of feeder lines 15, 16 of the measuring capacitor which would distort the capacitance measurement on measuring capacitor 14 also alter the measurement by the auxiliary capacitor formed by feeder lines 17, 18. The amount of interference may be determined by the change in capacitance, and the interference in the measurement on the measuring capacitor may be compensated. This may become important, for example, when sensor system 4 is immersed so deeply into fluid 2 that feeder lines 15, 16, 17, 18 are partially immersed in the fluid and thus the capacitance of the feeder lines is significantly increased.

Due to this compensation, which takes place in a compensation device 5a of first computing unit 5, the measurement of the dielectric constant of the fluid becomes much less susceptible to error and does not depend on ideal handling of the sensor assembly. The measuring system may also be calibrated much less frequently in comparison with known measuring systems.

According to FIG. 3, feeder lines 15, 16 of the measuring capacitor and blind spur lines 17, 18 are arranged in alternation, but FIG. 4 shows an arrangement in which the two feeder lines of measuring capacitor 14 and the two blind spur lines (i.e. at least one blind spur line) of the auxiliary capacitor are arranged directly side-by-side. In some embodiments, the distance between the feeder lines may be selected in such a way that the total width of the feeder lines running side-by-side and in parallel corresponds approximately to the width of measuring capacitor 14.

In contrast, FIG. 5 shows an arrangement in which the feeder lines of measuring capacitor 14 are arranged directly side-by-side and the spur lines are also arranged directly side-by-side and in parallel, but all four lines run in very close mutual proximity and in parallel, resulting in an increase in the feeder line capacitance. Therefore, the arrangement is more sensitive, for example, to whether the sensor is immersed so deeply in the fluid that the feeder lines are already surrounded by the fluid.

A temperature sensor 19 in the form of a temperature element is shown schematically as an example at the end of ceramic substrate 13 illustrated in FIG. 5. This temperature sensor measures the temperature of the fluid in the immediate vicinity of measuring capacitor 14 when the latter is immersed. Temperature sensor 19 is connected to analyzer device 4 by two feeder lines, which run on the back side of ceramic substrate 13 and are not shown in the figure, and are in turn connected to second computing device 6 for determining the temperature.

The feeder lines shown in FIGS. 3, 4 and 5 end at the end of ceramic substrate 13 each with widened printed conductor segments 20 which may function as plug contacts for a plug to be attached there, forming the end of a flexible cable whose other end is connected to analyzer device 4. The flexible cable may be appropriately shielded to prevent influences on the capacitance of the feeder lines of the capacitors.

Short measuring times, high measuring accuracy and a reduced calibration expense in determination of dielectric properties of oils, in particular deep-frying fats, are provided by the measuring system depicted here in combination with the sensor system used for this purpose. However, the measuring device may also be used in determining other quantities of fluids associated with the dielectric constant. This is not limited to liquids but instead it may also be used in gases, e.g., insulating gases for electric facilities. For example, use of a measuring device as depicted here in monitoring the quality of motor oil in motor vehicles is also conceivable as a mass-produced product. The driver of the vehicle may then be notified by a light on the dashboard not only as a function of the engine performance but also according to the actual quality measurement of the motor oil.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A measuring system for determining a property of an oil from a dielectric property of the oil, comprising:
    a first sensor for measuring an electric capacitance and a second sensor for measuring a temperature, wherein the first sensor is designed as a dielectric sensor which is immersed in the oil and has a stray-field capacitor which functions as the measuring capacitor, and the second sensor is designed as a temperature sensor which is immersed in the oil; and
    a compensation device for correcting the measured value of the electric capacitance, taking into account a capacitance reference value measured on an auxiliary capacitor situated in proximity to the measuring capacitor, wherein the corrected measured value of the electric capacitance and the temperature measured by the second sensor are used to determine an ageing state of the oil, wherein the dielectric sensor includes the auxiliary capacitor and on introduction of the dielectric sensor into the oil, the auxiliary capacitor is not immersed in the oil until the measuring capacitor is fully immersed in the oil, wherein feeder lines of the measuring capacitor and the auxiliary capacitor are identical in design and are arranged in mutual symmetry.

2. A measuring system for determining a property of an oil from a dielectric property of the oil, comprising:
    a first sensor for measuring an electric capacitance and a second sensor for measuring a temperature, wherein the first sensor is designed as a dielectric sensor which is immersed in the oil and has a stray-field capacitor which functions as the measuring capacitor, and the second sensor is designed as a temperature sensor which is immersed in the oil; and
    a compensation device for correcting the measured value of the electric capacitance, taking into account a capacitance reference value measured on an auxiliary capacitor situated in proximity to the measuring capacitor, wherein the corrected measured value of the electric capacitance and the temperature measured by the second sensor are used to determine an ageing state of the oil, wherein the dielectric sensor includes the auxiliary capacitor and on introduction of the dielectric sensor into the oil, the auxiliary capacitor is not immersed in the oil until the measuring capacitor is fully immersed in the oil, wherein the auxiliary capacitor is composed of at least one spur line which ends upstream from the measuring capacitor and is designed and arranged like the feeder lines of the measuring capacitor.

3. The measuring system as recited in claim 1, wherein the measuring capacitor is formed by a plurality of flat printed conductors in the form of interdigital capacitor.

4. The measuring system as recited in claim 3, wherein the printed conductors are printed on an insulating substrate by thin-film or thick-film methods.

5. The measuring system as recited in claim 1, wherein the temperature sensor is at least one of: a Negative Temperature Coefficient (NTC) resistor, a Positive Temperature Coefficient (PTC) resistor and a temperature element.

6. The measuring system as recited in claim 1, wherein the temperature sensor is connected to the dielectric sensor to form a structural unit.

7. The measuring system as recited in claim 4, wherein feeder lines leading to the temperature sensor are applied to the insulating substrate in the form of printed conductors.

8. The measuring system as recited in claim 6, wherein feeder lines leading to the temperature sensor are applied to an insulating substrate in the form of printed conductors.

9. A measuring system for determining a property of an oil from a dielectric property of the oil, comprising:
    a first sensor for measuring an electric capacitance and a second sensor for measuring a temperature, wherein the first sensor is designed as a dielectric sensor which is immersed in the oil and has a stray-field capacitor which functions as a measuring capacitor, and the second sensor is designed as a temperature sensor which is immersed in the oil, and wherein the first and second sensors are each connected to an analyzer device which assigns a value of the property to be determined to a measured temperature value and a measured electric capacitance value, wherein the property to be determined includes an ageing state of the oil, and wherein the value of the electric capacitance measured by the dielectric sensor is compared in a comparator device of the analyzer device with a stored reference value assigned to the measured temperature value, and a signal is output as a function of whether the reference value is reached or exceeded, wherein the dielectric sensor has an auxiliary capacitor and on introduction of the dielectric sensor into the oil, the auxiliary capacitor is not immersed in the oil until the measuring capacitor is fully immersed in the oil, and wherein feeder lines of the measuring capacitor and the auxiliary capacitor are identical in design and are arranged in mutual symmetry, wherein the auxiliary capacitor is composed of at least one spur line which ends upstream from the measuring capacitor and is designed and arranged like the feeder lines of the measuring capacitor, wherein the measuring capacitor is formed by a plurality of flat printed conductors in particular in the form of interdigital capacitor, and wherein the printed conductors are printed on an insulating substrate by thin-film or thick-film methods.

10. A measuring device, comprising:
a first sensor that measures a first property of an oil and outputs a first measured value;
a second sensor that measures a second property of said oil and outputs a second measured value;
an analyzer device connected to said first and second sensors, wherein said analyzer device compares said first and second measured values with stored reference values and outputs at least one signal based on differentials between said measured values and said stored reference values, wherein the at least one signal determines an ageing state of the oil; and
a compensation device that takes calibrating measurements of said first and second properties, wherein said compensation device is an auxiliary capacitor disposed in proximity to said first sensor, and wherein said auxiliary capacitor includes at least one spur line ending upstream from feeder lines of a measuring capacitor of said first sensor and that is symmetrical with the feeder lines of said measuring capacitor.

11. The measuring device of claim 10, where said first sensor is structurally attached to said second sensor.

12. The measuring device according to claim 10, wherein the oil is a deep-frying fat.

13. The measuring device according to claim 10, wherein the analysis device allocates a value of a characteristic to be determined to a measured temperature value and to a measured electrical capacitance value.

14. The measuring device according to claim 13, wherein the analysis device includes a comparison device, wherein the value of the electrical capacitance measured by a dielectric sensor is compared with a stored reference value allocated to the measured temperature value and a signal is output as a function of reaching or exceeding the reference value.

15. The measuring device according to claim 10, wherein supply lines of the measurement capacitor and supply lines of the auxiliary capacitor are formed symmetrically and identical to each other in construction.

16. The measuring device according to claim 10, wherein the auxiliary capacitor includes two stub cables ending in front of the measurement capacitor which are formed and arranged in a same way as supply lines of the measurement capacitor.

17. The measuring device according to claim 10, wherein the measurement capacitor is formed by a plurality of flat conductor tracks.

18. The measuring device according to claim 17, wherein the plurality of flat conductor tracks are formed as an interdigital capacitor.

19. The measuring device according to claim 17, wherein the plurality of flat conductor tracks are printed in thin or thick layer technology onto an insulated carrier.

20. The measuring device according to claim 19, wherein supply lines of a temperature sensor are applied to the insulating carrier in the form of conductor tracks.

21. The measuring device according to claim 10, wherein said first sensor includes a dielectric sensor and said first property is a capacitance of the oil, and said second sensor includes a temperature sensor and said second property is a temperature of the oil.

22. The measurement device according to claim 21, wherein the temperature sensor is at least one of: a Negative Temperature Coefficient (NTC) resistor, a Positive Temperature Coefficient (PTC) resistor and a temperature element.

23. The measuring system as recited in claim 2, wherein the measuring capacitor is formed by a plurality of flat printed conductors in the form of interdigital capacitor.

24. The measuring system as recited in claim 23, wherein the printed conductors are printed on an insulating substrate by thin-film or thick-film methods.

25. The measuring system as recited in claim 2, wherein the temperature sensor is at least one of: a Negative Temperature Coefficient (NTC) resistor, a Positive Temperature Coefficient (PTC) resistor and a temperature element.

26. The measuring system as recited in claim 2, wherein the temperature sensor is connected to the dielectric sensor to form a structural unit.

27. The measuring system as recited in claim 2, wherein feeder lines leading to the temperature sensor are applied to an insulating substrate in the form of printed conductors.

28. The measuring system according to claim 9, wherein the analysis device includes a comparison device, wherein the value of the electrical capacitance measured by the dielectric sensor is compared with a stored reference value allocated to the measured temperature value and a signal is output as a function of reaching or exceeding the reference value.

29. The measuring system according to claim 9, wherein supply lines of the measurement capacitor and supply lines of the auxiliary capacitor are formed symmetrically and identical to each other in construction.

30. The measuring system according to claim 9, wherein supply lines of the temperature sensor are applied to an insulating carrier in the form of conductor tracks.

31. The measuring system according to claim 9, wherein the temperature sensor is at least one of: a Negative Temperature Coefficient (NTC) resistor, a Positive Temperature Coefficient (PTC) resistor and a temperature element.

32. The measuring system according to claim 9, wherein the temperature sensor is connected with the dielectric sensor to form a structural unit.

* * * * *